United States Patent [19]

Fraenkel et al.

[11] Patent Number: 4,593,137

[45] Date of Patent: Jun. 3, 1986

[54] PARA-SELECTIVE AND BETA-SELECTIVE CRYSTALLIZED GLASS ZEOLITE ALKYLATION CATALYST

[75] Inventors: Dan Fraenkel; Moshe Levy; Margaret Cherniavsky, all of Rehovot, Israel

[73] Assignee: Yeda Research and Development Co., Ltd., Rehovot, Israel

[21] Appl. No.: 592,795

[22] Filed: Mar. 23, 1984

[30] Foreign Application Priority Data

Mar. 30, 1983 [IL] Israel ........................................ 68265

[51] Int. Cl.$^4$ ............................................... C07C 2/68
[52] U.S. Cl. .......................................... 585/467; 502/60
[58] Field of Search .......................................... 585/467

[56] References Cited

U.S. PATENT DOCUMENTS

| | | | |
|---|---|---|---|
| 4,268,420 | 5/1981 | Klotz | 585/467 |
| 4,292,457 | 9/1981 | Klotz | 585/467 |
| 4,482,774 | 11/1984 | Koetsier | 585/467 |
| 4,491,678 | 1/1985 | Oda et al. | 585/467 |

OTHER PUBLICATIONS

Trademark No. 115,846 3-13-17.
Trademark No. 198,173 5-5-25.
Trademark No. 336,044 6-23-36.
Trademark No. 417,987 11-27-45.

*Primary Examiner*—Curtis R. Davis
*Attorney, Agent, or Firm*—Browdy and Neimark

[57] ABSTRACT

Crystallized borosilicate glass zeolites prepared from a PYREX/template reaction system exhibit high para-selective and beta-selective catalytic activity in the respective alkylations of benzene, naphthalene, and derivatives thereof. A PYREX/tetraalkylammonium hydroxide system for alkylation of toluene with $C_1$–$C_3$-alkanols is exemplary.

9 Claims, 6 Drawing Figures

PARA-SELECTIVE AND BETA-SELECTIVE CRYSTALLIZED GLASS ZEOLITE ALKYLATION CATALYST

FIELD OF THE INVENTION

This invention relates to novel crystallized glasses and methods for their preparation and modification. Particularly, this invention relates to novel crystallized glasses possessing catalytic properties for hydrocarbon conversion reactions. More specifically, this invention relates to the preparation and modification of crystallized glass catalysts exhibiting high para-selectivity in the alkylation of aromatics and high beta-selectivity in the alkylation of naphthalenics, and especially exhibiting very high para-selectivity in the alkylation of toluene with $C_1$-$C_3$ aliphatic alcohols.

DESCRIPTION OF PRIOR ART

Molecular sieve aluminosilicates, known as zeolites, are effective catalysts in a variety of hydrocarbon conversion reactions. Several types of molecular sieves characterized by a high silica-to-alumina ratio (Si:Al$\geq$5), such as zeolite Y and mordenite in their acidic form are effective catalysts in aromatic hydrocarbon alkylation. For example, zeolite catalyzed toluene alkylation is present in U.S. Pat. No. 3,965,208; U.S. Pat. No. 4,100,215: U.S. Pat. No. 4,127,616; Yashima et al., *J. Catalysis*, 16, 273 (1970); E. Biron, Ph. D. Thesis, 1975, The Weizmann Inst. of Sci. In particular, the latter reference deals with the alkylation of toluene with $C_1$-$C_3$ aliphatic alcohols.

Due to the pore structure of zeolites which is made of uniform channels characterized by effective openings ranging between ca. 5 and ca. 10 Å, zeolite catalysts possess shape-selective properties. In the alkylation of toluene, for instance, where ortho, meta and para alkyltoluene isomers are produced, there is strong preference in some modified zeolites for the formation of the para isomer since this isomer has the smallest cross-sectional diameter enabling it to diffuse more easily through the zeolite channels, as compared with the other isomers.

Recently, high-siliceous pentasil zeolites with effective pore diameters in the 5-6 Å range have been synthesized by Mobil Oil Corp. e.g., U.S. Pat. No. 3,702,886 describing the preparation of the so-called ZSM5. These aluminosilicates show dramatic catalytic activity with exceptionally high thermal stability and aging resistability in the methylation (e.g. Kaeding et al., *J. Catalysis*, 67, 159 (1981); Brit. Pat. No. 1,574,523; U.S. Pat. No. 3,965,207; U.S. Pat. No. 4,250,345; U.S. Pat. No. 4,034,053), ethylation (e.g., U.S. Pat. No. 4,143,084; U.S. Pat. No. 4,117,024) and transalkylation (disproportionation) (e.g., Kaeding et al., *J. Catalysis*, 69, 392 (1981); U.S. Pat. No. 4,067,920) of toluene. They, however, fail to show substantial para-selectivity in their native ("as synthesized") state, as further exemplified, for instance, in L. B. Young et al., *J. Catalysis*, 76, 418 (1982), and become para-selective only after a certain modification, such as impregnation with a metal or non-metal element in a selcted form. The form of the element could be acid, e.g., phosphoric acid and boric acid, a salt, e.g. magnesium acetate, an organic compound, e.g., triphenylphosphine, or a polymer, e.g., a carboraneslioxane polymer.

The impregnated zeolite finally undergoes calcination at an elevated temperature, typically in the 400°-600° C. range. The following example illustrates the foregoing general description. According to this example, published in *J. Catalysis*, 67, 159 (1981), the unmodified, "as synthesized" zeolite was entirely unselective in toluene methylation with methyl alcohol at 400°-495° C. providing a thermodynamic equilibrium composition of xylene-23-4% para, 53-4% meta and 22-4% ortho (ibid., Table 4). By contrast, the same zeolite after modification with phosphoric acid produced at 600° C. a xylene mixture of 97% para-xylene (ibid., Table 8). In most other cases reported so far the para-selectivity is smaller and typically below 90%, e.g., U.S. Pat. No. 4,034,053.

A recent patent by DuPont, U.S. Pat. No. 4,283,306, describes a novel crystallized silica catalyzing the methylation of toluene to yield 51-56% para-xylene in its isomer mixture, which crystallized silica becomes extremely para-selective upon modification by impregnation with certain compounds. For example, impregnation with boric acid or with a solution of ethyl-orthosilicate and trifluoroacetic acid in toluene, has provided after calcination catalyst samples with which as high as 99% para-xylene could be produced in the methylation of toluene at 500°-550° C. using 10:1, toluene:methanol mole ratio, the toluene conversion being 8-9%.

In contrast with the prior art as described heretofore, novel silicate catalysts are prepared by crystallizing boro-silicate glasses of the type sold as PYREX, in the presence of a template such as a tetraalkylammonium hydroxide; these catalysts in their "as made" form are highly shape-selective in acid catalyzed reactions and, in particular, highly para-selective in the alkylation of toluene. Para-selectivity exceeding 90% is typical and as high as 99% para-selectivity is obtained after catalyst modification by impregnation with metal salt and/or non-metal compounds. Previous zeolite preparations from glasses, e.g., U.S. Pat. No. 3,714,366 (Fukuda et al.) U.S. Pat. No. 4,211,756 (Johnson), Can. 1,142,905 (Marosi), French 1,586,496 (Bayer), and others, do not disclose the reaction of PYREX glass with the presently disclosed templates to afford a highly para-selective catalyst.

SUMMARY OF THE INVENTION

The present invention provides crystallized glass zeolite catalysts for the selective p-position alkylation of benzene compounds and beta-position alkylation of naphthalene compounds having essentially an XRD spectrum as set out in the following Table 3 (Example 3); while the XRD is characteristic, it is not definitive of the zeolites of the present invention. It further provides such catalysts which are modified by impregnation with magnesium and phosphorus.

There is also provided a process for preparing selective crystallized glass zeolite catalysts for the p-selective alkylation of benzene type compounds and $\beta$-selective alkylation of naphthalene type compounds with $C_1$-$C_3$-alkanols or olefins, which comprises reacting a source of PYREX with a suitable template at elevated temperatures. Si and Al from non-PYREX sources may be added to the reaction system, if desired.

There is also provided a process of preferred para-position alkylation and beta-position alkylation of benzene and naphthalene derivatives, respectively, which comprises reacting the substrate with alkylation agent while passing the substrate and alkylation agent through a catalyst-loaded column at an elevated temperature.

Preferred substrates are toluene and naphthalene, and preferred alkylation agents are $C_1$-$C_3$-alkanols.

DETAILED DESCRIPTION OF THE INVENTION

According to the invention, a crystallized glass zeolite is prepared by reacting a source of borosilicate glass with a template of the type conventionally employed in the synthesis of ZSM5 catalysts. Borosilicate glasses having a boric oxide content of up to about 15% and a thermal expansion coefficient of less than about 40 ($\times 10^{-7}$/°C.) are typical.

Suitable borosilicate glasses broadly comprise the low-expansion commercial borosilicate glasses generally available under the trademark PYREX, such as PYREX Glass Codes 7720, 7740 (81% $SiO_2$, 13% $B_2O_3$, 4% $Na_2O$, 2% $Al_2O_3$ and 0.5% $K_2O$) and 7760, manufactured by Corning Glass Works, Corning, N.Y. Sources of PYREX which are useful in the process of the invention include PYREX powders, particles, and containers such as PYREX ampoules into which the template can be introduced. Other sources of PYREX such as PYREX-lined autoclaves may be suitable; however, conditions must be appropriate to obtain the desired reaction. Powders of 80-100 mesh (Tyler) and smaller are very reactive, but may cause a too-rapid change in the pH of the reaction mixture, and not leave sufficient time for an adequate high-pH nucleation which precedes crystallization; otherwise, when conditions are set to preserve very high pH throughout the entire catalyst preparation process, too small zeolite crystals may be formed which are less p-selective in catalytic alkylation.

Templates useful in the process of the present invention broadly include tetraalkylammonium hydroxides such as tetra-propylammonium hydroxide (TPAH) and tetraethylammonium hydroxide (TEAH), or the corresponding chlorides, bromides, or iodides. Other templates such as 1,6-hexanediol or 1,6-hexanediamine(hexamethylenediamine) also function as templates. The templates may also be prepared in situ, e.g., from a starting mixture containing the corresponding trialkylamine, plus alkyl halide or alcohol. The templates may be merely added to a PYREX ampoule or other PYREX container and reacted under the disclosed process conditions to provide zeolites according to the invention. The most effective reaction system appears to comprise PYREX in combination with TPAH, preferably without added Si or Al from non-PYREX sources; the system is conventionally reacted in an autoclave lined with TEFLON or other inert materials.

According to the process of the invention, the PYREX-template reaction system is reacted at an initial nucleation pH of $\geq 13$ at temperature of from about 100° to 200° C. for a period of time of at least 1 hour, and usually up to about 7 days, depending on the effectiveness of the PYREX base leach. Larger PYREX particles will generally require more time than powders to effect the reaction; temperatures of from about 140° C. to about 160° C. for from about 3 to 7 days, will generally suffice, with temperatures of about 152° C.±2° C. for 5 days being usual. Broadly, a ratio (w/w) of about 1:1 to 2:1 PYREX to TPAH or other template, and preferably about 1.5:1, will give the desired product. Exemplary proportions are given in Table 1, infra.

As previously noted, the crystallized glass zeolite of the invention may be modified during production by addition of, e.g. Si or Al from non-PYREX sources, or may be modified after preparation by impregnation with compounds of P, Mg, B, or similar atoms in ways conventionally known in the art. However, while prior-art catalysts such as those of Kaeding, et al., supra, require such post-preparation treatment to attain the desired selectivity, the modification of the zeolite of the invention is not necessary; excellent characteristic selectivity and activity is obtained with native (as synthesized) zeolites.

Generally, the zeolites of the invention are finished by drying and heating to 540° C. to evacuate the microcrystalline pores and channels from water and TPAH molecules, and calcine the remaining aluminosilicate product. The range of temperatures for effective decomposition of TPAH and calcining is 450°-650° C. The preferred range is 500°-600° C. To become catalytically active in alkylation, the calcined zeolite has to be converted to its hydrogen form, e.g., via its ammonium form. Ammonium ion exchange can be performed using a solution of ammonium ion such as salts, preferably ammonium chloride, nitrate or sulfate. The hydrogen form of the zeolite is then obtained by heating to a desired temperature in the range of 450°-550° C. for a period typically in the range of 0.1-10 hours, commonly between 1 and 3 hours, to decompose the ammonium ion according to the equation $$NH_4^+\text{-zeo}^- \rightarrow H^+\text{-zeo}^- + NH_3 \uparrow.$$

Instead of this indirect proton exchange, a direct exchange can be performed using acids, particularly inorganic acids, such as hydrochloric acids, nitric acid, sulfuric acid or others in dilute solutions.

The zeolites of the invention are characteized by a high para-selectivity without modification (note, for example, Example 17, infra). The X-ray diffraction (XRD) data for the inventive zeolites do not appear definitive; note for example, Examples 3 and 12 infra, wherein the XRD are similar, but para-selectivity of the respective zeolites differs widely (Example 13). Para-selectivity of the zeolites appears to be dependent upon the use of PYREX glass, as an identical mixture of oxides (not glassed) fails to provide adequate results (Example 40).

TABLE 1

| | Catalyst Preparation | | |
|---|---|---|---|
| | Favorable | More favorable | Most favorable |
| Ingredient Composition | | | |
| (1) In Teflon lined and unlined autoclave: | | | |
| Ratio | | | |
| PYREX*/TPAH, g/g | 0.5-2.0 | 1.0-1.5 | ≈1.5 |
| $H_2O$/TPAH, g/g | 2.0-3.0 | 2.2-2.8 | 2.5 |
| mol/mol | 22.7-34.0 | 24.9-31.7 | 28.3 |
| $B_2O_3$/TPAH, mol/mol | 0-0.6 | | |

TABLE 1-continued

| | Catalyst Preparation | | |
|---|---|---|---|
| | Favorable | More favorable | Most favorable |
| (2) In Pyrex ampules: | | | |
| Ratio, mol/mol | | | |
| $Al_2O_3$/TPAH | 0–0.6 | | |
| $SiO_2$/TPAH | 0–6.8 | 1.0–2.5 | ≈1.7 |
| NaOH/TPAH | 0–0.15 | | |
| $H_2O$/TPAH | 20–35 | 25–30 | 28 |
| Reaction Conditions | | | |
| Temperature, °C. | 100–200 | 140–160 | 152 ± 2 |
| Time, h | 1–240 | 72–168 | ≈120 |

*As powder.

The following Examples illustrate the invention, which Examples are to be construed in a non-limitative manner.

EXAMPLE 1

Figure 1B:
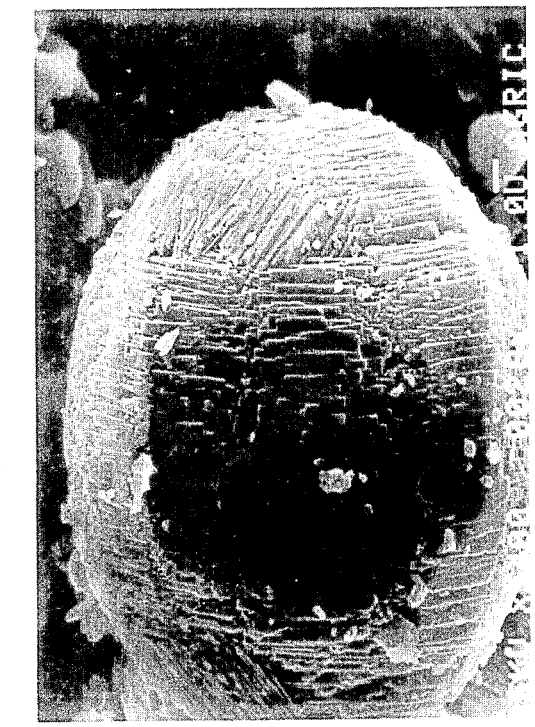
FIGS. 1a-1d illustrate electron micrographs of the catalyst obtained in Example 3, showing an assembly of large particles (FIG. 1a), two different clusters of crystals (FIGS. 1b and 1c) and an isolated large crystallite (FIG. 1d)
Figure 1D:
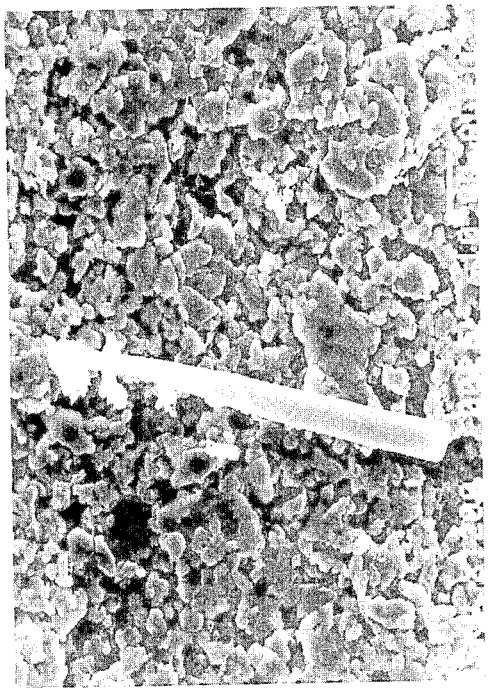
Figure 1A:
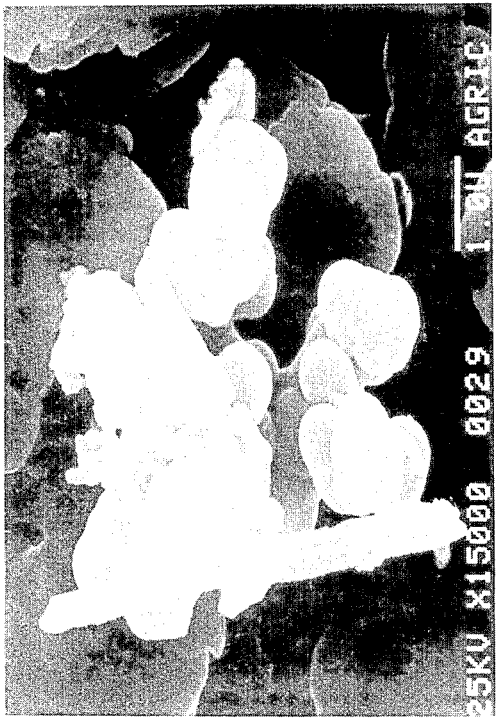
Figure 1C:
Figure 2A:
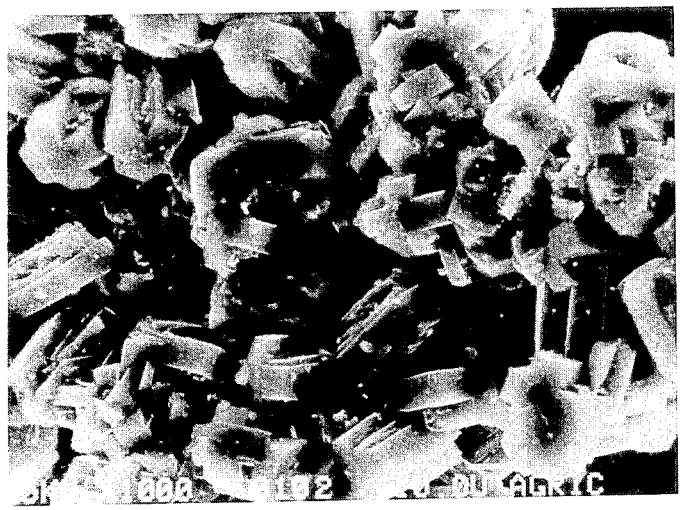
FIGS. 2a and 2b illustrate electron micrographs of the catalyst obtained in Example 1; interpenetrant 10 μm crystals twinned crosswise are seen clearly in FIGS. 2a and 2b.
Figure 2B:
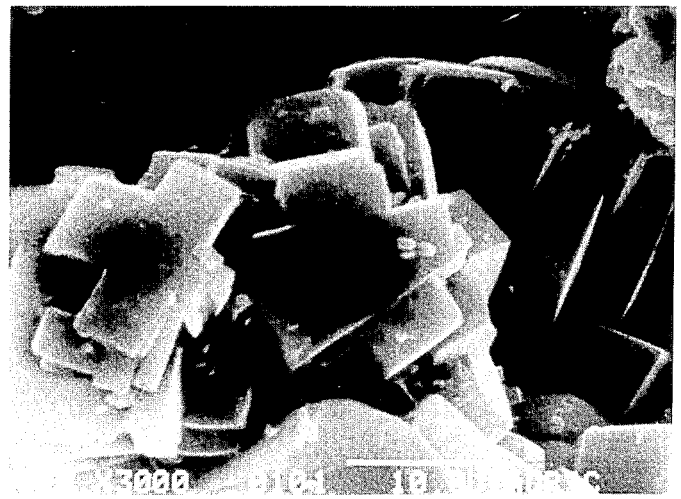

A PYREX ampule (I.D.—12.5 mm; E.D.—20.0 mm) was filled with 10.9 g of tetrapropylammonium hydroxide (TPAH) solution obtained by evaporation of 15.6 g of a standard 20% solution (Fluka 88110). The ampule was sealed and heated to 152° C. for 5 days. After 2.5 h of heating the liquid in the tube became turbid with some precipitate. After 17.5 h an extensive attack of the PYREX was observed. An organic phase separated above the aqueous solution. A considerable amount of colorless precipitate was formed which after shaking settled at the bottom of the ampule. This precipitate was found in higher yield after 41.5 h and after 65.5 hr it jammed the lower part of the ampule. The ampule then was opened and its content transferred to a filtration funnel. After filtration, repeated washing with deionized water, drying overnight at 120° C. and, finally, calcination at 540° C., 0.8 g solid was obtained. This solid was ion-exchanged twice with 1N ammonium chloride solution, then dried overnight at 120° C. FIG. 2 gives electron micrographs of this product showing large (normally, ≈(4–10)×(4–10)×(10–30)$\mu m^3$) crystals that typically couple crosswise.

EXAMPLE 2

This Example describes the effectiveness of the solid obtained in Example 1 as para-selective catalyst in the alkylation of toluene with methanol.

0.5 g of the solid catalyst mixed with 2.5 g glass beads was loaded between glass-wool stuffing in a 20 mm I.D. PYREX tubular reactor surrounded by electrical heater equipped with a thermoregulator. This catalyst mixture was first preactivated at 500° C. for 2 h under flow of air, 60 cc/min then at 450° C. for 0.5 h under Ar, 60 cc/min. Then, the temperature was reduced to 400° C. and, while the argon stream continued at the same rate, a feed of toluene:methanol (molar ratio, 2:1, respectively) was added from a Sage syringe pump model 341, placed on top of the reactor, at a rate of 2.1 ml per hour. Samples were taken periodically from the bottom exit of a cold-water condenser placed below the reactor. The samples were analyzed gas chromatographically on a Hewlett-Packard 7620A Gas Chromatograph having a thermal conductivity detector and equipped with CSI supergrator-3A programmable computing integrator. The column was a 6 m×3.2 mm stainless steel filled with 5% DC 550/10% Bentone 34 on 60–80 ChromW NAW. Results are summarized in Table 2.

The results in Table 2 show that the solid obtained in Example 1 is an efficient catalyst for the alkylation of toluene with methanol. Under the above conditions which are given only as illustration and by no means restricts the scope of the present invention, this catalyst does not deactivate for at least 3 h and during this period provides a xylene mixture in which the para isomer concentration is 87–90%.

TABLE 2

| Sample No. | 1 | 2 | 3 | 4 | 5 |
|---|---|---|---|---|---|
| Weight (g) | 1.0 | 1.7 | 1.8 | 1.8 | 1.7 |
| Time (min) | 50 | 110 | 170 | 230 | 290 |
| Toluene Conversion, % | 13.1 | 13.6 | 13.1 | 8.6 | 5. |
| Liquid product analysis, wt % | | | | | |
| benzene | 0.2 | — | 0.12 | — | — |
| toluene | 86.9 | 86.4 | 86.9 | 91.4 | 95. |
| p-xylene | 10.27 | 10.88 | 10.6 | 7.334 | 3.87 |
| m-xylene | 0.815 | 0.923 | 1.031 | 0.553 | 0.445 |
| o-xylene | 0.287 | 0.331 | 0.502 | 0.287 | 0.325 |
| p-ethyltoluene | 1.239 | 1.119 | 0.7 | 0.388 | 0.183 |
| m-ethyltoluene | 0.202 | 0.14 | — | — | — |
| Xylene isomer distribution, % | | | | | |
| p | 90.3 | 89.7 | 87.4 | 89.7 | 83.4 |
| m | 7.2 | 7.6 | 8.5 | 6.8 | 9.6 |
| o | 2.5 | 2.7 | 4.1 | 3.5 | 7.0 |

EXAMPLE 3

This example illustrates the effect of adding silica and alumina to the reaction mixture in the synthesis as described in Example 1.

6.2 g $SiO_2$ (Davison grade 950) was dissolved in 67.5 g of TPAH (as in Example 1) by gentle heating. The solution was evaporated to a final weight of 50 g. To this was added dropwise, under stirring, 1.35 g of a solution of sodium aluminate prepared by dissolving 1.0 g aluminum (turnings), in a solution of 1.8 g NaOH (pellets, analytical, Merck) in 5.0 g $H_2O$, and evaporating to a final weight of 7.0 g. A gel was formed instantly and it was allowed to equilibrate with the solution for about 1 h. The obtained mixture was transferred into four identical PYREX ampules (as in Example 1) which, after sealing, were heated to 152° C. and kept at this temperature for 5 days. During this period the ampules were taken out of the oven twice daily and shaken well. Fine colorless crystals gradually formed during the first 2 days along with the separation of an organic layer above the aqueous reaction mixture. Later, the crystals became a colorless mass sticking to the ampule walls. This mass could not be removed by shaking. After 5 days, the ampules were cooled and opened and the contents of all four of them was combined and processed as in Example 1. The 15.0 g solid obtained after calcination was ion exchanged twice with 75 ml 1N NH4Cl solution for 2 h at ambient temperature to afford, after washing and drying at 120° C. overnight, 14.5 g of a pale gray powder. Based on the starting silica and alumina the solid contains 170% excess weight the source of which is the PYREX ampules. The ampules were indeed attacked strongly by the reactive solution during the 5 day heating period. XRD spectrum of the solid shows that the aluminosilicate obtained has a zeolite structure. The main spectral lines are given in Table 3. Chemical analyses: $SiO_2$, 87.4%; $Al_2O_3$, 3.5%; $Na_2O$, 0.2%.

TABLE 3

| X-ray diffraction data of aluminosilicate prepared in Example 3. | | | | | |
|---|---|---|---|---|---|
| 2θ* | d, Å | Rel. int.** | 2θ* | d, Å | Rel. int.** |
| 8.2 | 10.8 | s | 21.6 | 4.1 | m |
| 9.1 | 9.7 | s | 22.4 | 4.0 | vw |
| 14.2 | 6.2 | w | 23.4 | 3.8 | vs |
| 15.0 | 5.9 | w | 24.2 | 3.7 | s |
| 15.7 | 5.6 | w | 24.7 | 3.6 | s |
| 16.2 | 5.5 | w | 26.7 | 3.3 | vw |
| 18.0 | 4.9 | vw | 27.2 | 3.3 | w |
| 19.5 | 4.5 | vw | 27.7 | 3.2 | vw |
| 20.6 | 4.3 | vw | 29.5 | 3.0 | w |
| 21.1 | 4.2 | s | 30.2 | 3.0 | w |

*Copper $K\alpha_1$, $\lambda = 1.54050$.
**vs, very strong; s, strong; m, medium; w, weak; vw, very weak.

FIG. 1 gives typical electron micrographs of the crystallites obtained.

EXAMPLE 4

Following the conditions as in Example 2, the solid obtained in Example 3 was tested in the alkylation of toluene with methanol. Results are summarized in Table 4.

The similarity between Table 4 and Table 2 implies that the catalysts obtained in Examples 1 and 3 are essentially of the same activity and high para-selectivity in the alkylation of toluene with methanol. Thus, addition of silica and aluminate to the TPAH solution before heating in the sealed ampule does not appear to alter the catalytic performance of the solid obtained in Example 1.

TABLE 4

| Sample number | 1 | 2 | 3 | 4 | 5 | |
|---|---|---|---|---|---|---|
| Weight (g) | 0.5 | 1.2 | 1.4 | 1.7 | 1.8 | Σ6.6, yield 93% |
| Time (min) | 20 | 60 | 120 | 180 | 240 | |
| Toluene Conversion, % | 14.4 | 14.4 | 13.1 | 9.7 | 4.7 | |
| Liquid product analysis, wt % | | | | | | |
| benzene | 0.3 | 0.15 | 0.05 | — | — | |
| toluene | 85.6 | 85.6 | 86.9 | 90.3 | 95.3 | |
| p-xylene | 10.99 | 11.27 | 10.78 | 7.29 | 3.35 | |
| m-xylene | 0.82 | 0.87 | 0.76 | 0.59 | 0.35 | |
| o-xylene | 0.2 | 0.28 | 0.28 | 0.31 | 0.21 | |
| p-ethyltoluene | 1.64 | 1.31 | 0.73 | 0.45 | 0.4 | |
| m-ethyltoluene | 0.2 | 0.14 | 0.06 | 0.2 | 0.3 | |
| pseudocumene | 0.11 | 0.16 | 0.22 | 0.4 | | |
| Xylene isomer distribution, % | | | | | | |
| p | 91.5 | 90.7 | 91.2 | 89.0 | 85.7 | |
| m | 6.8 | 7.0 | 6.4 | 7.2 | 8.9 | |
| o | 1.7 | 2.3 | 2.4 | 3.8 | 5.4 | |

EXAMPLE 5

This Example illustrates the effectiveness of the catalyst obtained in Example 3 in the ethylation of toluene with ethanol.

1.0 g of catalyst activated at 500° C. for 2 h was mixed with 2.5 g glass beads and the mixture was loaded in the reactor as described in Example 2, and preactivated at 450° C. for 1.5 h under argon at a flow of 60 cc/min. The temperature was decreased to 350° C. and a toluene:ethanol feed (2:1 molar ratio, respectively) was introduced to the reactor as in Example 2. Reaction aliquots were taken and analyzed as in Example 2. Results are given in Table 5.

TABLE 5

| Sample number | 1 | 2 | 3 | 4 | 5 | 6 | |
|---|---|---|---|---|---|---|---|
| Weight (g) | 0.8 | 0.9 | 1.0 | 1.4 | 2.0 | 1.5 | Σ7.3, Total yield 82% |
| Time (min) | 35 | 75 | 120 | 180 | 230 | 300 | |
| Toluene conversion, % | 19.6 | 18.8 | 21.3 | 21.3 | 21.8 | 21.4 | |
| Liquid product analysis, wt % | | | | | | | |
| benzene | 0.6 | 0.3 | 0.2 | 0.1 | 0.06 | 0.04 | |
| toluene | 80.4 | 81.2 | 78.7 | 78.7 | 78.2 | 78.6 | |
| ethylbenzene | 1.2 | 0.8 | 0.6 | 0.4 | 0.3 | 0.22 | |
| p-xylene | 1.825 | 1.349 | 0.938 | 0.674 | 0.438 | 0.344 | |
| m-xylene | 0.135 | 0.113 | 0.084 | 0.067 | 0.05 | 0.05 | |
| o-xylene | a | a | 0.011 | a | a | a | |
| p-ethyltoluene | 13.21 | 14.12 | 17.02 | 17.77 | 18.32 | 18.68 | |
| m-ethyltoluene | 1.477 | 1.358 | 1.672 | 1.716 | 1.83 | 1.764 | |
| o-ethyltoluene | 0.209 | 0.05 | 0.1 | 0.017 | 0.137 | 0.034 | |
| b | 0.4 | 0.2 | 0.4 | 0.350 | 0.52 | 0.151 | |
| Ethyltoluene isomer distribution, % | | | | | | | |
| p | 88.7 | 90.9 | 90.6 | 91.1 | 90.3 | 91.2 | |
| m | 9.9 | 8.7 | 8.9 | 8.8 | 9.0 | 8.6 | |

TABLE 5-continued

| Sample number | 1 | 2 | 3 | 4 | 5 | 6 |
|---|---|---|---|---|---|---|
| o | 1.4 | 0.3 | 0.5 | 0.1 | 0.7 | 0.2 |

[a] undetectable.
[b] unidentified

As seen in Table 5, at the chosen conditions which are to be considered only as an example, steady state is approached during the first hour on stream and no deactivation is noted after 5 h on stream. Toluene conversion is ≈20% and the yield of ethyltoluene is improving during the run while the initially formed xylene is gradually disappearing. The percent of para isomer in ethyltoluene is 89–91.

EXAMPLES 6–10

These Examples are given to demonstrate the effectiveness of the solid obtained in Example 3 as paraselective catalyst in the isopropylation of toluene.

In Example 6, 1.0 g of the solid catalyst mixed with 2.5 g glass beads was placed in the reactor as in Example 2 and activated at 450° C. for 1.5 h, then at 500° C. for 1 h under air (≈30 cc per min) and finally at 400° C. for 0.5 h under argon (≈60 cm/min). The temperature was decreased to 250° C. and a toluene:iso-propanol mixture (10:1 molar ratio, respectively) was fed into the reactor as in Example 2, at a rate of 4.4 ml/h.

Samples were taken and analyzed as in Example 2 and the results are summarized in Table 6.

TABLE 6

| Sample number | 1 | 2 | 3 | 4 | 5 | 6 |
|---|---|---|---|---|---|---|
| Weight (g) | 1 | 3 | 5 | 6.2 | 8.6 | 10.1 |
| Time (min) | 20 | 75 | 120 | 170 | 220 | 280 |
| Rate (ml/h) | 4.4 | 4.4 | 8.8 | 8.8 | 13.0 | 13.0 |
| Liquid product analysis, wt % | | | | | | |
| <$C_6$ | 0.38 | 0.35 | 0.46 | 0.4 | 0.45 | 0.32 |
| toluene | 98.1 | 97.8 | 97.9 | 98.0 | 98.1 | 98.2 |
| p-cymene | 0.355 | 0.532 | 0.642 | 0.747 | 0.833 | 0.942 |
| m-cymene | 0.002 | 0.003 | 0.004 | 0.005 | 0.005 | ≈0.006 |
| p-propyltoluene | 0.733 | 0.840 | 0.622 | 0.505 | 0.370 | 0.278 |
| m-propyltoluene | 0.01 | 0.015 | 0.009 | 0.008 | 0.006 | 0.005 |
| $C_4$-toluene | 0.045 | 0.054 | 0.062 | 0.029 | 0.035 | 0.038 |
| $C_5$-toluene | 0.115 | 0.135 | 0.12 | 0.082 | 0.056 | 0.040 |
| Cymene isomer distribution, %: | | | | | | |
| p | 99.4 | 99.3 | 99.4 | 99.3 | 99.3 | 99.3 |
| m | 0.6 | 0.7 | 0.6 | 0.7 | 0.7 | 0.7 |
| Propyltoluene isomer distribution, %: | | | | | | |
| p | 98.6 | 98.5 | 98.6 | 98.4 | 98.3 | 98.2 |
| m | 1.4 | 1.5 | 1.4 | 1.6 | 1.7 | 1.8 |

As seen in Table 6, the catalyst prepared in Example 3 is active in the production of alkyltoluenes in the reaction of toluene with iso-propanol. The main product after long onstream time is para-cymene and its positional isomeric purity of >99% throughout the entire run is unprecedented with other catalysts even at the rather low conversion achieved (≈2%).

In Example 7 the effect of increasing the conversion in the above reaction is shown. 3.0 g of catalyst as obtained in Example 3 was loaded in the reactor described in Example 2 in the following order: 15 mm glass wool, 35 mm PYREX balls (d=5 mm), 10 mm glass wool, 20 mm zeolite powder, 15 mm glass wool and 50 mm PYREX balls. Activation was done at 500° C. for 2 h under air (≈80 cc/min), then at 400° C. for 0.5 h under argon (≈60 cc/min). After decreasing the temperature to 200° C. a toluene:i-propanol, 2:1 molar mixture was fed into the reactor at a rate of 0.7 ml per hour. Samples were taken periodically and analyzed. Results are presented in Table 7.

Table 7 shows that a three-fold increase in conversion was achieved in this run with high selectivity to cymene, but the para-selectivity was appreciably lower than in the former Example.

Example 8 shows the effects of toluene-to-isopropanol ratio, space velocity and temperature on the catalytic efficiency in the isopropylation of toluene. After 290 minutes on stream the experiment described in Example 7 was stopped and the reactor was allowed to cool overnight. Then, the reactor was reheated to 500° C. for 2 h under air (≈80 cc/min) and reactivated at 400° C. for additional 0.5 h under argon (≈60 cc/min). The temperature was reduced to 200° C. and a 6:1, toluene:iso-propanol mixture was fed into the reactor at 4.4 ml per hour for 145 min. Then, the temperature was raised to 250° C. for an additional period of 135 minutes. Samples were taken periodically and analyzed as in Example 2. The results are summarized in Table 8.

TABLE 7

| Sample number | 1 | 2 | 3 |
|---|---|---|---|
| Weight (g) | 0.4 | 0.4 | 0.2 |
| Time (min) | 75–165 | 240 | 290 |
| Toluene conversion, mol % | 3 | 2.7 | 3.2 |
| Liquid product analysis, wt % | | | |
| <$C_6$ | 1.97 | 2.46 | 1.04 |
| toluene | 94.1 | 94.2 | 94.9 |
| ethylbenzene | 0.02 | 0.04 | 0.03 |
| p-xylene | 0.04 | 0.04 | 0.09 |
| m-xylene | 0.06 | 0.03 | 0.08 |
| o-xylene | 0.08 | 0.07 | — |
| ethyltoluene | 0.07 | 0.02 | — |
| p-cymene | 2.596 | 2.375 | 3.065 |
| m-cymene | 0.159 | 0.193 | 0.344 |
| o-cymene | 0.003 | 0.002 | 0.003 |
| p-propyltoluene | 0.4 | 0.28 | 0.29 |
| m-propyltoluene | — | — | — |
| butyltoluene | 0.3 | 0.3 | 0.12 |
| Cymene isomer distribution, %: | | | |

TABLE 7-continued

| Sample number | 1 | 2 | 3 |
|---|---|---|---|
| p | 94.13 | 92.44 | 89.85 |
| m | 5.80 | 7.50 | 10.08 |
| o | 0.07 | 0.06 | 0.07 |

TABLE 8

| Sample number | 1 | 2 | 3 | 4 | 5 | 6 |
|---|---|---|---|---|---|---|
| Weight (g) | 1.1 | 3.5 | 3.0 | 2.5 | 2.5 | 3.2 |
| Time (min) | 30 | 95 | 145 | 185 | 230 | 280 |
| Temperature | 200 | 200 | 200 | 250 | 250 | 250 |
| Liquid product analysis, wt % | | | | | | |
| <$C_6$ | 1.12 | 0.95 | 0.5 | 1.61 | 2.15 | 1.86 |
| toluene | 95.0 | 97.8 | 98.1 | 90.4 | 92.4 | 91.4 |
| p-xylene | 0.005 | 0.006 | 0.12 | 0.348 | 0.19 | 0.11 |
| m-xylene | 0.002 | 0.002 | 0.09 | 0.067 | 0.12 | 0.03 |
| o-xylene | n.d.[a] | n.d. | n.d. | n.d. | n.d. | n.d. |
| ethyltoluene | n.d. | n.d. | n.d. | 0.3 | 0.32 | 0.3 |
| p-cymene | 2.902 | 0.886 | 0.677 | 2.114 | 2.845 | 3.50 |
| m-cymene | 0.192 | 0.198 | 0.310 | 0.159 | 0.15 | 0.15 |
| o-cymene | n.d. | 0.004 | 0.133 | n.d. | n.d. | n.d. |
| p-propyltoluene | 0.36 | n.d. | n.d. | 1.505 | 2.84 | 1.44 |
| m-propyltoluene | 0.022 | n.d. | n.d. | 0.15 | 0.15 | 0.093 |
| $C_4$-toluene | 0.2 | n.d. | n.d. | 1.7 | 0.2 | 0.6 |
| $C_5$-toluene | 0.14 | n.d. | n.d. | 1.2 | 0.2 | 0.6 |
| Cymene isomer distribution, % | | | | | | |
| p | 93.8 | 81.4 | 60.4 | 93.0 | 95.0 | 95.9 |
| m | 6.2 | 18.2 | 27.7 | 7.0 | 5.0 | 4.1 |
| o | 0.0 | 0.4 | 11.9 | 0.0 | 0.0 | 0.0 |

[a]non-detectable.

According to Table 8, when the toluene-to-isopropanol ratio was increased to 6 and the feed flow rate to 4.4 ml/h there was rapid deactivation with loss of para-selectivity at 200° C., but after the temperature has been raised to 250° C. catalytic activity and para-selectivity were restored.

Example 9 shows the effect of catalyst regeneration (with regard to Example 6) on the isopropylation of toluene. The reaction described in the preceding Example 8 was stopped and the reactor cooled overnight. Regeneration was performed at 500° C. for 9 h under air ($\approx$60 cc/min) and followed by preactivation at 400° C. for 1 h under argon ($\approx$60 cc/min). After lowering of the temperature to 250° C. a 10:1, toluene:i-propanol feed was introduced into the reactor at a rate of 13 ml per hour. Samples were taken periodically during 730 min and analyzed as in Example 2. Results are given in Table 9. It is seen that during the entire period of the run (12 h) a constant conversion and selectivity were obtained. Toward the end of the run $\approx$6% of the toluene was converted (our of 10% theoretical) and the principal product, para-cymene, was 96% isomer-pure.

Clearly, the catalyst in Example 9 is more active than the catalyst in Example 6.

Example 10 demonstrates the effect of increasing the temperature to 275° C. and replacing iso-propanol by normal-propanol on the conversion of toluene to cymene and propyltoluene. The reaction described in the above Example 9 was stopped and the catalytic reactor cooled to ambient temperature during 16 h. Catalyst regeneration was then repeated at 500° C. for 18 h under air ($\approx$60 cc/min). Afterwards, the reaction was continued as in the preceeding paragraph, but at 275° C., for an additional period of 580 minutes. After 460 min on stream, isopropanol was replaced by n-propanol.

TABLE 9

| Sample No. | 1 | 2 | 3 | 4 | 5 | 6 | 7 | 8 | 9 | 10 | 11 | 12 |
|---|---|---|---|---|---|---|---|---|---|---|---|---|
| Weight (g) | 9.1 | 10.3 | 7.6 | 12.0 | 10.3 | 17 | 12.1 | 11.9 | 8.2 | 10.1 | 14 | 9.0 |
| Time (min) | 50 | 110 | 155 | 225 | 285 | 380 | 440 | 500 | 545 | 605 | 680 | 730 |
| Liquid product analysis, wt % | | | | | | | | | | | | |
| <$C_6$ | 1.27 | 1.29 | 1.34 | 0.97 | 0.7 | 0.75 | 0.92 | 0.7 | 0.8 | 0.7 | 0.7 | 0.5 |
| toluene | 93.4 | 92.6 | 92.3 | 93.1 | 91.8 | 92.5 | 92.2 | 92.3 | 92.3 | 92.5 | 92.7 | 92.3 |
| p-cymene | 2.278 | 4.035 | 4.612 | 4.693 | 4.952 | 5.341 | 5.444 | 5.589 | 5.490 | 5.692 | 5.43 | 5.74 |
| m-cymene | 0.0657 | 0.099 | 0.058 | 0.078 | 0.153 | 0.075 | 0.155 | 0.082 | 0.176 | 0.104 | 0.19 | 0.09 |
| p-propyltoluene | 1.412 | 1.01 | 0.84 | 0.705 | 0.79 | 0.74 | 0.776 | 0.7 | 0.661 | 0.560 | 0.55 | 0.55 |
| m-propyltoluene | 0.179 | 0.07 | 0.06 | 0.065 | 0.07 | 0.06 | 0.067 | — | 0.057 | 0.016 | 0.047 | 0.048 |
| $C_4$-toluene | 0.393 | 0.32 | 0.32 | 0.25 | 0.25 | 0.21 | 0.18 | 0.18 | 0.18 | 0.13 | — | 0.12 |
| $C_5$-toluene | 0.469 | 0.34 | 0.22 | 0.03 | 0.05 | 0.16 | 0.14 | 0.1 | — | 0.1 | — | 0.08 |
| Cymene isomer: distribution, % | | | | | | | | | | | | |
| p | 97.1 | 97.2 | 97.0 | 97.2 | 97.0 | 97.0 | 97.2 | 96.9 | 96.9 | 96.9 | 96.6 | 96.0 |
| m | 2.9 | 2.8 | 3.0 | 2.8 | 3.0 | 3.0 | 2.8 | 3.1 | 3.1 | 3.3 | 3.4 | 4.0 |
| Propyltoluene isomer distribution, % | | | | | | | | | | | | |
| p | 88.7 | 93.5 | 93.3 | 91.6 | 91.8 | 92.5 | 92.1 | 92.4 | 92.1 | 91.8 | 92.1 | 92.0 |
| m | 11.3 | 6.5 | 6.7 | 8.4 | 8.2 | 7.5 | 7.9 | 7.6 | 7.9 | 8.2 | 7.9 | 8.0 |

Results are summarized in Table 10.

TABLE 10

| Sample No. | 1 | 2 | 3 | 4 | 5 | 6 | 7 | 8 |
|---|---|---|---|---|---|---|---|---|
| Weight (g) | 1.3 | 1.2 | 1.0 | 1.1 | 1.1 | 1.0 | 2.0 | 1.1 |
| Time (min) | 15–85 | 180 | 290 | 395 | 455 | 460 | 525 | 580 |
| ROH | i-propanol | → | → | → | → | n-propanol | → | → |
| Liquid product analysis, wt % | | | | | | | | |
| propanol | — | — | — | — | — | — | 5.8 | 5.6 |
| <$C_6$ | 1.03 | 1.04 | 1.12 | 1.21 | 0.97 | 5.83 | 2.0 | 1.38 |
| toluene | 92.8 | 92.4 | 92.6 | 91.5 | 92.1 | 87.0 | 90.6 | 91.5 |
| p-cymene | 2.661 | 3.468 | 3.897 | 4.589 | 4.313 | 4.631 | 0.627 | 0.744 |
| m-cymene | 0.071 | 0.044 | 0.106 | 0.05 | 0.141 | 0.075 | 0.093 | 0.137 |
| p-propyltoluene | 1.677 | 1.764 | 1.517 | 1.525 | 1.397 | 1.523 | 0.244 | 0.275 |
| m-propyltoluene | 0.184 | 0.168 | 0.139 | 0.151 | 0.145 | 0.160 | — | — |
| $C_4$-toluene | 0.31 | 0.39 | 0.31 | 0.31 | 0.27 | 0.31 | 0.18 | 0.19 |
| $C_5$-toluene | 0.42 | 0.47 | 0.33 | 0.32 | 0.31 | 0.27 | 0.2 | — |
| Cymene isomer distribution, % | | | | | | | | |
| p | 97.4 | 97.4 | 97.4 | 97.2 | 96.8 | 96.7 | 87.1 | 84.4 |
| m | 2.6 | 2.6 | 2.6 | 2.8 | 3.2 | 3.3 | 12.9 | 15.6 |
| Propyltoluene isomer distribution, % | | | | | | | | |
| p | 90.0 | 91.3 | 91.6 | 90.9 | 90.6 | 90.5 | 81.3 | 79.7 |
| m | 10.0 | 8.7 | 8.4 | 9.1 | 9.4 | 9.5 | 18.7 | 20.3 |

According to Table 10, the higher temperature employed causes only slight reduction in the yield of cymene in favor of propyltoluene. Replacement of isopropanol by normal-propanol causes almost immediate decrease in conversion to ≈1% with substantial decrease in para-selectivity (from 97 to 84% in the case of cymene).

EXAMPLE 11

This Example demonstrates the potential of the solid catalyst as obtained in Example 3 in the production of cresol from phenol and methanol.

1.0 g of catalyst mixed with 2.5 g glass beads was activated in the reactor as described in Example 2 at 500° C. for 2 h under air (≈30 cc/min), then at 450° C. for 0.5 h under argon (≈60 cc/min). The temperature was lowered to 400° C. and a phenol:methanol mixture (2:1 molar ratio, respectively) was fed into the reactor at a rate of 2.1 ml/h. Samples were taken periodically and analyzed gas chromatographically as in Example 2 using a 2 m×2 mm glass column filled with Carbopack C/0.1% SP 1000. Results are presented in Table 11. As seen, the above catalyst is reactive in converting toluene to cresol but exhibits fast deactivation. Only at low conversion substantial para-selectivity as achieved.

TABLE 11

| Sample number | 1 | 2 | 3 | 4 |
|---|---|---|---|---|
| Weight (g) | 0.7 | 0.9 | 2.1 | 2.3 |
| Time (min) | 30 | 70 | 145 | 230 |
| Liquid (arenol) product analysis, wt % | | | | |
| phenol | 93.2 | 96.3 | 97.6 | 98.0 |
| anisol | 0.6 | — | 1.06 | 1.5 |

TABLE 11-continued

| Sample number | 1 | 2 | 3 | 4 |
|---|---|---|---|---|
| o-cresol | 2.424 | 1.333 | 0.211 | 0.177 |
| m-cresol | 1.009 | 0.411 | 0.044 | 0.047 |
| p-cresol | 2.366 | 1.652 | 0.346 | 0.276 |
| dimethylphenol (?) | 0.32 | 0.22 | 0.17 | 0.11 |
| Cresol isomer distribution, % | | | | |
| p | 41.8 | 39.2 | 35.1 | 35.5 |
| m | 17.4 | 12.1 | 7.3 | 9.4 |
| o | 40.8 | 48.6 | 57.6 | 55.1 |

COMPARATIVE EXAMPLE 12

This Example describes a synthesis of a crystalline aluminosilicate according to Example 3 but in the absence of PYREX glass.

A gel was prepared as in Example 3. After equilibration it was transferred to a Teflon-lined autoclave which was placed in the oven, at a temperature of 152° C., for 5 days. The reaction mixture was then processed exactly as in Example 3 to give after calcination 5.5 g of white powder. This material was exchanged twice with 25 ml of 1N NH$_4$Cl solution for 2 h at ambient temperature, washed and dried overnight at 120° C. The XRD spectrum of the obtained aluminosilicate product is very similar to that of the product in Example 3.

Chemical analysis: $SiO_2$, 84.1%; $Al_2O_3$, 7.1%; $Na_2O$, 0.37%.

EXAMPLE 13

Following the conditions as in Example 2, the solid obtained in Example 12 was tested in the alkylation of toluene with methanol. Results are summarized in Table 12.

TABLE 12

| Sample number | 1 | 2 | 3 | 4 | 5 | 6 | 7 |
|---|---|---|---|---|---|---|---|
| Weight (g) | 0.4 | 1.0 | 1.3 | 1.0 | 2.0 | 1.8 | 1.0 |
| Time (min) | 15 | 55 | 105 | 145 | 205 | 265 | 300 |
| Toluene Conversion, % | 26.9 | 22.7 | 22.9 | 24.0 | 24.9 | 23.6 | 24.5 |
| Liquid product analysis, wt % | | | | | | | |
| benzene | 0.3 | 0.3 | 0.2 | 0.2 | 0.2 | 0.11 | 0.09 |
| toluene | 73.1 | 77.3 | 77.1 | 76.0 | 75.1 | 76.4 | 75.5 |
| p-xylene | 11.81 | 11.88 | 12.04 | 12.21 | 13.33 | 12.35 | 12.75 |
| m-xylene | 5.55 | 5.48 | 5.70 | 5.81 | 4.76 | 5.76 | 5.81 |

TABLE 12-continued

| Sample number | 1 | 2 | 3 | 4 | 5 | 6 | 7 |
|---|---|---|---|---|---|---|---|
| o-xylene | 1.77 | 1.78 | 1.87 | 1.97 | 1.66 | 2.09 | 2.14 |
| p-ethyltoluene | 4.7 | 1.51 | 1.3 | 1.3 | 1.5 | 1.2 | 1.24 |
| m-ethyltoluene | 1.96 | 0.92 | 0.78 | 0.75 | 1.1 | 0.7 | 0.7 |
| pseudocumene | 0.6 | 0.7 | 0.82 | 1.1 | 1.8 | 1.4 | 1.6 |
| Xylene isomer distribution, % | | | | | | | |
| p | 61.7 | 62.0 | 61.4 | 61.1 | 67.5 | 61.1 | 61.6 |
| m | 29.0 | 28.6 | 29.1 | 29.1 | 24.1 | 28.5 | 28.1 |
| o | 9.3 | 9.3 | 9.5 | 9.8 | 8.4 | 10.3 | 10.3 |

Comparing Table 12 with Tables 2 and 4 reveals that the catalysts prepared from PYREX glass are appreciably more para-selective in the alkylation of toluene with methanol than the catalyst prepared in the absence of PYREX glass.

EXAMPLE 14

The catalyst obtained in Example 12 was further tested in the alkylation of toluene with ethanol according to the procedure described in Example 5, but with 0.5 g catalyst (instead of 1.0 g). Results are summarized in Table 13.

TABLE 13

| Sample number | 1 | 2 | 3 | 4 | 5 | 6 |
|---|---|---|---|---|---|---|
| Weight (g) | 0.5 | 1.3 | 1.7 | 1.8 | 1.9 | 1.5 |
| Time (min) | 15 | 60 | 120 | 130 | 240 | 300 |
| Toluene conversion, % | 23.7 | 30.9 | 32.3 | 32.8 | 33.3 | 34.1 |
| Liquid product analysis, wt % | | | | | | |
| benzene | 0.5 | 0.32 | 0.23 | 0.21 | 0.18 | 0.15 |
| toluene | 76.3 | 69.1 | 67.7 | 67.2 | 66.7 | 65.9 |
| ethylbenzene | 0.89 | 0.8 | 0.7 | 0.6 | 0.5 | 0.5 |
| p-xylene | 0.65 | 0.62 | 0.51 | 0.46 | 0.40 | 0.40 |
| m-xylene | 0.47 | 0.42 | 0.37 | 0.31 | 0.23 | 0.27 |
| o-xylene | 0.13 | 0.13 | 0.10 | 0.09 | 0.06 | 0.07 |
| p-ethyltoluene | 11.05 | 14.4 | 15.36 | 15.58 | 16.03 | 16.44 |
| m-ethyltoluene | 9.35 | 13.47 | 14.29 | 14.72 | 15.12 | 15.46 |
| o-ethyltoluene | $a$ | $a$ | $a$ | $a$ | $a$ | 0.07 |
| $\Sigma^b$ | — | 0.5 | 0.5 | 0.6 | 0.5 | 0.5 |
| Ethyltoluene isomer distribution, % | | | | | | |
| p | 54.2 | 51.7 | 51.8 | 51.4 | 51.5 | 51.4 |
| m | 45.8 | 48.3 | 48.2 | 48.6 | 48.5 | 48.4 |
| o | — | — | — | — | — | 0.2 |

$a$ undetectable.
$b$ unidentified.

Comparison between Table 13 and Table 5 shows that the catalyst prepared from PYREX glass is much more para-selective in the alkylation of toluene with ethanol than the catalyst prepared in the absence of PYREX glass.

EXAMPLE 15

The catalyst obtained in Example 12 was also tested in the alkylation of phenol with methanol according to Example 11, but with 0.5 g catalyst (instead of 1.0 g). Results are presented in Table 14.

TABLE 14

| Sample number | 1 | 2 | 3 |
|---|---|---|---|
| Weight (g) | 0.2 | 1.5 | 1.0 |
| Time (min) | 20 | 80 | 120 |
| Liquid (arenol) product analysis, wt % | | | |
| phenol | 88.7 | 90.5 | 87.2 |
| anisol | — | 2.0 | 2.9 |
| o-cresol | 4.8 | 3.74 | 3.07 |
| m-cresol | 3.6 | 1.53 | 0.94 |
| p-cresol | 2.8 | 2.05 | 2.02 |
| Cresol isomer distribution, %: | | | |
| p | 25 | 28 | 33 |

TABLE 14-continued

| Sample number | 1 | 2 | 3 |
|---|---|---|---|
| m | 32 | 21 | 16 |
| o | 43 | 51 | 51 |

Comparing Table 14 with Table 11 shows that the catalyst prepared from PYREX glass is more para-selective in the alkylation of phenol with methanol than the catalyst prepared in the absence of PYREX glass.

EXAMPLE 16

This Example describes the modification of the zeolite catalysts obtained in Examples 3 and 12 by impregnation with phosphorus and magnesium following a procedure as described in U.S. Pat. No. 4,250,345. To a solution of 2.12 g 85% $H_3PO_4$ in 3.03 g water 2.97 g of the crystalline material from Example 3 or 12 was added. The obtained mixture was allowed to equilibrate overnight at ambient temperature. The mixture was then filtered and the solid was dried at 120° C. for 3 h, then calcined at 500° C. for 3 h to give 3.0 g of a phosphorous modified material. This solid was added to a solution of 7.5 g magnesium acetate tetrahydrate in 6.0 g water. The mixture was allowed to equilibrate overnight at ambient temperature, then filtered and the obtained solid was dried at 120° C. and calcined at 500° C. for 3 h to give 3.27 g of a magnesium-phosphorous modified material designated PMg-I in the case of the catalyst from Example 3, and PMg-II in the case of the catalyst from example 12.

EXAMPLE 17

To show the effect of modification by impregnation with P and Mg on the para-selectivity, the modified catalysts PMg-I and PMg-II were tested in the alkylation of toluene with methanol and with ethanol.

Selected results of the alkylation of toluene with methanol are given in Table 15 which compares modified with the corresponding unmodified catalysts.

TABLE 15

| Sample | Cat. from Example 3 (I) | PMg-I | Cat. from Example 12 (II) | PMg-II |
|---|---|---|---|---|
| Time on stream, min | 120 | 60 | 300 | 95 |
| Toluene conversion, % | 11 | 3.1 | 21 | 0.6 |
| Selectivity to xylene, wt % | 91 | 86 | 83 | 70 |
| Xylene isomer distribution, % | | | | |
| p | 91.2 | 98.3 | 61.6 | 81.8 |
| m | 6.4 | 1.6 | 28.1 | 14.6 |
| o | 2.4 | 0.1 | 10.3 | 3.6 |
| % ethylbenzene in p-xylene | | 1.1 | | 11.5 |

Reaction conditions: T = 400° C., WHSV = 3.9, tol: methanol = 2:1 (molar ratio).

It is seen that under comparable conditions the modification improves the para-selectivity in both cases but the gap between I and II remains. PMg-I is a much better para-selective catalyst in the alkylation of toluene with methanol (giving >98% p-xylene at toluene conversion of 3%) than PMg-II (which at 5-fold smaller toluene conversion gives only 82% p-xylene).

In the alkylation of toluene with ethanol according to the procedure presented in Example 5, both PMg-I and PMg-II afforded 100% isomer-pure para-ethyltoluene. Table 16 lists yield of this product as function of time on stream. PMg-I is shown to be a more effective and more stable catalyst for the production of para-ethyltoluene than PMg-II.

TABLE 16

| Time on stream, hours | wt % para-ethyltoluene | |
|---|---|---|
| | PMg-I | PMg-II |
| 0.5 | 5.2 | 1.8 |
| 1.0 | 5.4 | 1.5 |
| 2.0 | 5.6 | 1.1 |
| 3.0 | 5.6 | 1.0 |
| 4.0 | 5.5 | 0.8 |
| 5.0 | 4.8 | 0.7 |

EXAMPLE 18

This Example illustrates the use of PYREX glass particles as starting material in the synthesis of p-selective zeolite catalysts. 50 g of tetrapropylammonium hydroxide (20%) was evaporated to a final weight of 35 g. This solution and 36.6 g of Pyrex glass in the form of half cylinders, 20 mm by length and of 4 mm thickness, were introduced into a TEFLON lined autoclave. The closed autoclave was heated to 150° C. and kept at this temperature for 120 h. Afterwards, the autoclave was opened and its contents filtered, washed and dried overnight at 120° C. To the crystalline material obtained, crystals scraped from the half cylinders were added to give an overall yield of 2.8 g. The crystalline material obtained was calcined then exchanged with an ammonium chloride solution as in Example 1. This material gives an x-ray diffraction spectrum and scanning electron micrographs practically identical with those of the material obtained in Example 1. The weight difference between the cylinders before and after reaction was 3.8 g.

EXAMPLES 19-22

These Examples demonstrate the use of variable amounts of PYREX powder having particle size in the 0.08-0.125 mm range in the synthesis of p-selective alkylation catalysts. All syntheses followed the procedure as described in Example 18 except for the use of Pyrex powder instead of the half cylinder particles.

In Example 19, 5 g PYREX powder as starting material gave before calcination 4.5 g of crystalline powder. The calcined and ammonium exchanged product had XRD spectrum and electron micrographs essentially identical with those of the materials obtained in Examples 1 and 18.

In Examples 20-22, 10 g, 15 g and 20 g PYREX powder, respectively, were used in the catalyst synthesis.

EXAMPLES 23-26

Four identical runs, according to Example 2, were done to show the effectiveness of the catalysts prepared in Examples 19-22 in the alkylation of toluene with methanol. Example 23 is the catalytic run with the solid product obtained in Example 19. Examples 24-26 relate similarly to the catalysts obtained in Examples 20-22, respectively. Table 17 summarizes the effect of varying the amount of PYREX glass in the catalyst synthesis upon the catalytic performance.

Table 17 shows that while no effect of the amount of PYREX powder is observed in the 5-10 g range, as more PYREX powder is used in the catalyst synthesis in the range of 10-20 g, conversion decreases and p-selectivity increases. However, the decrease in conversion occurs mainly between 15 and 20 g whereas the increase in p-selectivity is seen between 10 and 15 g. Therefore the sample obtained in the synthesis with 15 g Pyrex (Example 21) appears to bear optimal catalytic performance.

TABLE 17

| Example | 23 | 24 | 25 | 26 |
|---|---|---|---|---|
| Amount of Pyrex powder in catalyst synthesis (g) | 5 | 10 | 15 | 20 |
| Pyrex-to-TPAH ratio (g/g) | 0.5 | 1.0 | 1.5 | 2.0 |
| Sample number | 3 | 2 | 2 | 2 |
| Weight (g) | 1.5 | 2.4 | 1.2 | 1.3 |
| Time (min) | 60-120 | 30-130 | 40-100 | 35-95 |
| Toluene conversion, % | 17.1 | 17.6 | 16.4 | 5.7 |
| Liquid product analysis, wt % | | | | |
| <$C_6$ | — | — | 0.37 | 0.1 |
| benzene | 0.63 | 0.11 | 6.06 | — |
| toluene | 82.9 | 82.4 | 83.64 | 94.3 |
| ethylbenzene | 0.14 | — | — | 0.05 |
| p-xylene | 9.98 | 11.06 | 12.55 | 4.89 |
| m-xylene | 2.85 | 2.72 | 0.84 | 0.27 |
| o-xylene | 0.86 | 1.00 | 0.36 | 0.12 |
| p-ethyltoluene | 1.73 | 1.33 | 1.42 | 0.22 |
| m-ethyltoluene | 0.66 | 0.52 | 0.26 | 0.004 |

| TABLE 17-continued | | | | |
|---|---|---|---|---|
| Example | 23 | 24 | 25 | 26 |
| pseudocumene | 0.29 | 0.54 | 0.32 | 0.03 |
| Xylene isomer distribution, % | | | | |
| p | 72.8 | 74.8 | 91.2 | 92.6 |
| m | 20.8 | 18.4 | 6.1 | 5.0 |
| o | 6.4 | 6.8 | 2.7 | 2.4 |
| Ethylbenzene in toluene, % | 1.4 | — | — | 1.0 |

EXAMPLE 27-29

In these Examples p-selective catalysts were prepared from PYREX powder, TPAH and $B_2O_3$ in TEFLON lined autoclave. The procedure was as in Examples 19–22.

Table 18 summarizes the compositions of starting materials in these syntheses.

TABLE 18

| Example | TPAH,* g | PYREX powder, g | $B_2O_3$, g |
|---|---|---|---|
| 27 | 35 | 5 | 1.3 |
| 28 | 35 | 10 | 2.0 |
| 29 | 35 | 15 | 1.1 |

*Solution after evaporation, see Example 18.

EXAMPLES 30–37

The performance of the catalysts obtained in Examples 27–29 in the alkylation of toluene with methanol is demonstrated in Examples 30–37 which followed the procedure as given in Example 2. Table 19 summarizes results of these runs and shows the effect of addition of $B_2O_3$ to the synthesis mixture, the effect of toluene-to-methanol (molar) ratio and the effect of the reaction temperature.

According to Table 19 there is no substantial effect of the addition of $B_2O_3$ on the liquid product obtained in the alkylation of toluene with methanol. At 400° C., the p-selectivity ranges from 75 to 90% and the toluene conversion from ≈9 to ≈18%. At toluene-to-methanol ratio of 1:1, increasing the temperature from 400° to 500° C. causes increase in conversion with no substantial effect on the para-selectivity. At 500° C. with the catalyst of Example 29, changing the toluene-to-methanol ratio from 1:1 (Example 34) through 4:1 (Example 36*) to 6:1 (Example 37) causes increase in both activity (as toluene conversion, percent of theoretical) and para-selectivity.

TABLE 19

| Example | 30 | 31 | 32 | 33 | 34 | 35 | 36 | 36* | 37 |
|---|---|---|---|---|---|---|---|---|---|
| Catalyst Preparation Example | 27 | 27 | 28 | 29 | 29 | 29 | 29 | 29 | 29 |
| Toluene: methanol molar ratio | 1:1 | 2:1 | 2:1 | 1:1 | 1:1 | 2:1 | 4:1 | 4:1 | 6:1 |
| Temperature (°C.) | 500 | 400 | 400 | 400 | 500 | 400 | 400 | 500 | 500 |
| Sample number | 2 | 2 | 2 | 2 | 2 | 2 | 2 | 4 | 2 |
| Weight, (g) | 1.4 | 1.4 | 1.7 | 1.5 | 1.5 | 1.5 | 1.5 | 3.0 | 1.5 |
| Time (min) | 30–90 | 30–90 | 35–95 | 90–150 | 30–90 | 30–90 | 30–90 | 135–255 | 30–90 |
| Toluene conversion, % mol | 29.7 | 15.2 | 8.7 | 17.6 | 22.9 | 14.0 | 11.0 | 8.1 | 6.2 |
| (percent of theoretical) | (30) | (30) | (17) | (18) | (23) | (28) | (44) | (32) | (38) |
| Liquid product analysis, wt % | | | | | | | | | |
| <$C_6$ | 0.2 | 0.07 | 0.1 | 0.6 | 0.3 | 0.23 | 0.15 | 0.1 | 0.05 |
| benzene | 0.22 | 0.06 | 0.02 | 0.1 | — | 0.15 | 0.2 | 0.06 | 0.6 |
| toluene | 66.8 | 82.3 | 89.8 | 78.8 | 73.4 | 83.7 | 87.0 | 90.6 | 92.9 |
| ethylbenzene | — | 0.04 | 0.003 | — | — | 0.04 | 0.03 | 0.04 | 0.02 |
| p-xylene | 22.36 | 11.65 | 8.29 | 13.7 | 18.53 | 10.46 | 8.92 | 7.25 | 5.27 |
| m-xylene | 6.32 | 2.79 | 0.63 | 2.56 | 4.02 | 2.29 | 1.82 | 1.24 | 0.75 |
| o-xylene | 1.95 | 0.94 | 0.33 | 0.96 | 1.26 | 0.70 | 0.5 | 0.56 | 0.23 |
| p-ethyltoluene | 0.51 | 1.07 | 0.47 | 1.53 | 0.49 | 1.59 | 0.85 | 0.08 | 0.06 |
| m-ethyltoluene | 0.21 | 0.4 | 0.04 | 0.48 | 0.19 | 0.54 | 0.33 | 0.02 | 0.003 |
| pseudocumene | 1.44 | 0.53 | 0.25 | 0.93 | 1.29 | 0.3 | 0.19 | 0.08 | 0.11 |
| Xylene isomer distribution, % | | | | | | | | | |
| p | 73.0 | 75.7 | 89.6 | 79.5 | 77.8 | 77.7 | 79.3 | 80.2 | 84.2 |
| m | 20.6 | 18.1 | 6.8 | 14.9 | 16.9 | 17.0 | 16.2 | 13.7 | 12.0 |
| o | 6.4 | 6.1 | 3.6 | 5.6 | 5.3 | 5.3 | 4.5 | 6.1 | 3.8 |
| Ethylbenzene in toluene, % | — | 0.3 | 0.1 | — | — | 0.4 | 0.3 | 0.6 | 0.4 |

*Continuation of run 36. After 90 min on stream the temperature was raised from 400 to 500° C.

COMPARATIVE EXAMPLE 38

The importance of PYREX glass as starting material in the synthesis of the disclosed catalysts can be seen in this example describing a similar catalyst preparation using soda glass powder. The synthesis followed Example 21. 15 g soda glass powder were added to 62.5 g TPAH and the mixture was evaporated to final weight of 65 g. Heating in Teflon lined autoclave and the subsequent work up were performed as in the preceding Examples. The final catalyst obtained had XRD spectrum of less intense peaks but the same pattern as that of the catalyst obtained in Example 21 and poorer activity in toluene alkylation with methanol. Thus, at 400° C. with toluene-to-methanol ratio of 2:1 and flow rate of 2.1 ml/h 0.5 g of this catalyst gave after 35 min on stream toluene conversion of <2% and after 95 min on stream, ≈3.3%. By contrast, the catalyst from Example 21, prepared from PYREX glass, gave under similar conditions 19.2% toluene conversion after 40 min and 16.4% after 100 min on stream.

COMPARATIVE EXAMPLE 39

This Example describes the preparation of an alkylation catalyst from a mixture of oxides identical in composition with that of PYREX glass.

2.55 g NaOH and 0.3 g KOH were dissolved in 10 ml $H_2O$. 0.52 g aluminum turnings were added to this solution and allowed to react with the base until a clear solution was formed. The solution obtained was evaporated up to a final weight of 10 g.

A borosilicate solution was prepared by dissolving 4.0 g $SiO_2$ and 0.64 g $B_2O_3$ in 40.3 g TPAH (20% solution in water). This solution was evaporated to a final weight of 33.0 g.

1.0 g of the aluminate solution was added to the borosilicate solution under stirring. The mixture obtained containing some gel, was allowed to equilibrate for ≈1 h, then transferred to a TEFLON lined autoclave. Heating and the subsequent treatment were as in the previous Examples (e.g., Example 19).

EXAMPLE 40

The catalyst obtained in Example 39 was tested in the alkylation of toluene with methanol as in Example 2. Results are presented in Table 20.

According to Table 20, the catalyst of Example 39 has high activity but poor p-selectivity compared with catalysts prepared from PYREX glass, as can be seen in preceding Tables, e.g., Table 17.

EXAMPLES 41 AND 42

In these examples catalysts were prepared as in Example 39 but with more $B_2O_3$ in the synthesis mixture. In Example 41 the borosilicate solution contained 1.3 g of $B_2O_3$ and in Example 42, 2.4 g of $B_2O_3$.

EXAMPLES 43 AND 44

The catalysts prepared in Examples 41 and 42 were tested in the alkylation of toluene with methanol according to the conditions of Example 2. Results are presented in Table 21 for the catalyst of Example 41 and in Table 22 for the catalyst of Example 42.

TABLE 20

| Sample number | 1 | 2 | 3 | 4 | 5 |
|---|---|---|---|---|---|
| Weight, (g) | 0.6 | 1.5 | 1.6 | 1.8 | 1.6 |
| Time (min) | 0–25 | 25–80 | 80–140 | 140–210 | 210–270 |
| Toluene conversion, % | 25.7 | 26.5 | 25.6 | 24.3 | 25.4 |
| Liquid product analysis, wt % | | | | | |
| <$C_6$ | 0.9 | 0.33 | 0.36 | 0.4 | 0.4 |
| benzene | 1.0 | 0.82 | 0.6 | 0.7 | 0.61 |
| toluene | 74.3 | 73.5 | 74.4 | 75.7 | 74.6 |
| ethylbenzene | 0.21 | 0.18 | 0.17 | 0.12 | 0.09 |
| p-xylene | 8.31 | 8.78 | 9.15 | 7.61 | 7.06 |
| m-xylene | 8.03 | 8.26 | 8.75 | 7.95 | 7.4 |
| o-xylene | 2.76 | 2.79 | 1.81 | 2.73 | 2.82 |
| p-ethyltoluene | 1.58 | 1.68 | 1.82 | 1.59 | 2.85 |
| m-ethyltoluene | 1.96 | 1.89 | 1.87 | 1.83 | 2.8 |
| pseudocumene | 0.8 | 1.2 | 1.04 | 1.06 | 1.01 |
| Xylene isomer distribution, % | | | | | |
| p | 43.5 | 44.2 | 46.4 | 41.6 | 40.8 |
| m | 42.1 | 41.6 | 44.4 | 43.4 | 42.8 |
| o | 14.4 | 14.0 | 9.2 | 14.8 | 16.3 |
| Ethylbenzene in toluene, % | 2.5 | 2.0 | 1.8 | 1.6 | 1.3 |

TABLE 21

| Sample number | 1 | 2 | 3 | 4 | 5 |
|---|---|---|---|---|---|
| Weight, (g) | 0.3 | 1.6 | 1.7 | 1.7 | 1.6 |
| Time (min) | 0–20 | 20–80 | 80–140 | 140–200 | 200–260 |
| Toluene conversion, % | 21.9 | 29.5 | 29.8 | 29.4 | 28.8 |
| Liquid product analysis, wt % | | | | | |
| <$C_6$ | 0.4 | 0.4 | 0.3 | 0.3 | 0.2 |
| benzene | 1.2 | 1.4 | 1.1 | 0.9 | 0.7 |
| toluene | 78.1 | 70.5 | 70.2 | 70.6 | 71.2 |
| ethylbenzene | 0.15 | 0.21 | 0.18 | 0.14 | 0.09 |
| p-xylene | 6.07 | 7.48 | 8.08 | 8.3 | 8.51 |
| m-xylene | 8.14 | 11.26 | 11.38 | 11.1 | 10.82 |
| o-xylene | 3.1 | 4.72 | 4.85 | 4.65 | 4.45 |
| p-ethyltoluene | 0.79 | 1.01 | 1.16 | 1.04 | 0.92 |
| m-ethyltoluene | 1.28 | 1.78 | 1.51 | 1.55 | 1.45 |
| pseudocumene | 0.76 | 1.18 | 1.23 | 1.42 | 1.5 |
| Xylene isomer distribution, % | | | | | |
| p | 35.1 | 31.9 | 33.2 | 34.5 | 35.8 |
| m | 47.0 | 48.0 | 46.8 | 46.2 | 45.5 |
| o | 17.9 | 20.1 | 20.0 | 19.3 | 18.7 |
| Ethylbenzene in toluene, % | 2.4 | 2.7 | 2.2 | 1.6 | 1.1 |

TABLE 22

| Sample number | 1 | 2 | 3 | 4 | 5 |
|---|---|---|---|---|---|
| Weight, (g) | 0.8 | 1.0 | 1.6 | 2.5 | 1.6 |
| Time (min) | 0–30 | 30–60 | 60–120 | 120–205 | 205–265 |
| Toluene conversion, % | 18.0 | 20.8 | 20.8 | 20.8 | 20.8 |
| Liquid product analysis, wt % | | | | | |
| <$C_6$ | | | | | |
| benzene | 0.63 | 0.62 | 0.58 | 0.47 | 0.41 |
| toluene | 82.0 | 79.2 | 79.2 | 79.2 | 79.2 |
| ethylbenzene | 0.16 | 0.17 | 0.18 | 0.19 | 0.17 |
| p-xylene | 5.65 | 5.97 | 6.06 | 6.25 | 6.61 |
| m-xylene | 6.00 | 7.00 | 6.97 | 6.87 | 6.63 |
| o-xylene | 2.17 | 2.54 | 2.63 | 2.65 | 2.58 |
| p-ethyltoluene | 1.3 | 1.69 | 1.6 | 1.58 | 1.6 |
| m-ethyltoluene | 1.44 | 2.06 | 1.93 | 1.74 | 1.7 |
| pseudocumene | 0.6 | 0.7 | 0.85 | 0.98 | 1.01 |

TABLE 22-continued

| Sample number | 1 | 2 | 3 | 4 | 5 |
|---|---|---|---|---|---|
| Xylene isomer distribution, % | | | | | |
| p | 40.9 | 38.5 | 38.7 | 39.6 | 41.8 |
| m | 43.4 | 45.2 | 44.4 | 43.6 | 41.9 |
| o | 15.7 | 16.3 | 16.9 | 16.8 | 16.3 |
| Ethylbenzene in toluene, % | 2.8 | 2.9 | 2.8 | 2.9 | 2.5 |

From Tables 21 and 22 (and their comparison with Table 20) it appears that there is no clear effect of the concentration of $B_2O_3$ in the synthesis mixture on the performance of the catalyst in the alkylation of toluene with methanol. In the investigated range of $B_2O_3$ concentration in the inorganic oxide ingredients, namely between 13% and 36%, toluene conversion was between 20 and 30% and the para-selectivity between 32 and 46%. It is therefore, concluded that it is not the presence of $B_2O_3$ in the Pyrex glass which is responsible for the exceptional para-selectivity of the catalysts obtained when PYREX glass is reacted with tetrapropylammonium hydroxide according to the aforementioned Examples.

What is claimed is:

1. A method for the selective alkylation of toluene to p-alkyl toluene comprising alkylating toluene with a $C_1-C_3$-alkanol in the presence of a crystallized borosilicate glass zeolite alkylation catalyst para-selective in the alkylation of benzene or derivatives thereof and beta-selective in the alkylation of naphthalene or derivatives thereof.

2. A method of preferred p-position alkylation and beta-position alkylation of a substrate comprising benzene or naphthalene or a derivative thereof, respectively, comprising reacting the substrate with a $C_1-C_3$-alkanol or $C_2-C_3$-olefin alkylating agent while passing the substrate and alkylating agent through a column loaded with a crystallized borosilicate glass zeolite alkylation catalyst para-selective in the alkylation of benzene or derivatives thereof and beta-selective in the alkylation of naphthalene or derivatives thereof at an elevated temperature.

3. A process according to claim 2, wherein the substrate is toluene and the alkylating agent is a $C_1-C_3$-alkanol.

4. A process according to claim 2, wherein the substrate is toluene and the alkylating agent is ethylene.

5. A process according to claim 2, wherein the substrate is toluene and the alkylating agent is propylene.

6. A process according to claim 1 wherein said crystallized borosilicate glass zeolite alkylation catalyst has an X-ray diffraction pattern with its most intense peak at about 23.4.

7. The method of claim 2 wherein said crystallized borosilicate glass zeolite alkylation catalyst has an X-ray diffraction pattern with its most intense peak at about 23.4.

8. The method of claim 1 wherein said zeolite catalyst is crystallized from a reaction system comprising a source of borosilicate glass and a template of a tetraalkyl-ammonium hydroxide, chloride, iodide or bromide.

9. The method of claim 2 wherein said zeolite catalyst is crystallized from a reaction system comprising a source of borosilicate glass and a template of a tetraalkyl-ammonium hydroxide, chloride, iodide or bromide.

* * * * *